United States Patent [19]

Herrmann et al.

[11] Patent Number: 4,737,342

[45] Date of Patent: Apr. 12, 1988

[54] TEST MODULE

[75] Inventors: Raymond J. Herrmann, Westlake; Harry F. DeBevec, Elyria; Randolph F. Bradshaw, Avon; Peter O. Botten, North Ridgeville, all of Ohio

[73] Assignee: Ciba Corning Diagnostics Corp., Medfield, Mass.

[21] Appl. No.: 405,764

[22] Filed: Aug. 6, 1982

[51] Int. Cl.⁴ .............................................. G01N 35/06
[52] U.S. Cl. ......................................... 422/64; 422/67; 422/103
[58] Field of Search .............. 137/554, 624.13, 625.41; 364/416; 422/64, 65, 67, 68, 73, 103; 436/43, 47; 141/130, 186, 188

[56] References Cited

U.S. PATENT DOCUMENTS

| | | | |
|---|---|---|---|
| 3,449,959 | 6/1969 | Grimshaw | 422/64 X |
| 3,536,450 | 10/1970 | Dus et al. | 422/70 |
| 3,788,816 | 1/1974 | Rohrbaugh et al. | 422/64 |
| 3,802,782 | 4/1974 | Natelson | 422/65 X |
| 3,901,084 | 8/1975 | Brailsford | 141/130 X |
| 4,030,888 | 6/1977 | Yamamoto et al. | 422/67 |
| 4,058,367 | 11/1977 | Gilford | 364/416 X |
| 4,156,437 | 5/1979 | Chivens et al. | 137/554 |
| 4,315,891 | 2/1982 | Sakurada | 422/65 X |
| 4,322,216 | 3/1982 | Lillig et al. | 422/64 X |

FOREIGN PATENT DOCUMENTS 950703  7/1974  Canada .................................. 422/65

*Primary Examiner*—David L. Lacey
*Assistant Examiner*—Michael S. Gzybowski
*Attorney, Agent, or Firm*—Daniel Reitenbach

[57] ABSTRACT

A test module or reagent handling device for use with a clinical analyzer for conducting body serum assays and/or immunoassays; the test module coacting with the analyzer to selectively provide a plurality of liquid dilution and reagent materials to a serum sample, the test module having programmable valve means coacting with a dispense probe to serially: select a serum sample and to deposit said sample and liquid dilution material into a dilution cup or vessel; subsequentially withdraw a portion of the diluted serum from the dilution cup and to dispense said diluted serum portion along with at least one liquid reagent material into a reaction cup or vessel.

9 Claims, 2 Drawing Sheets

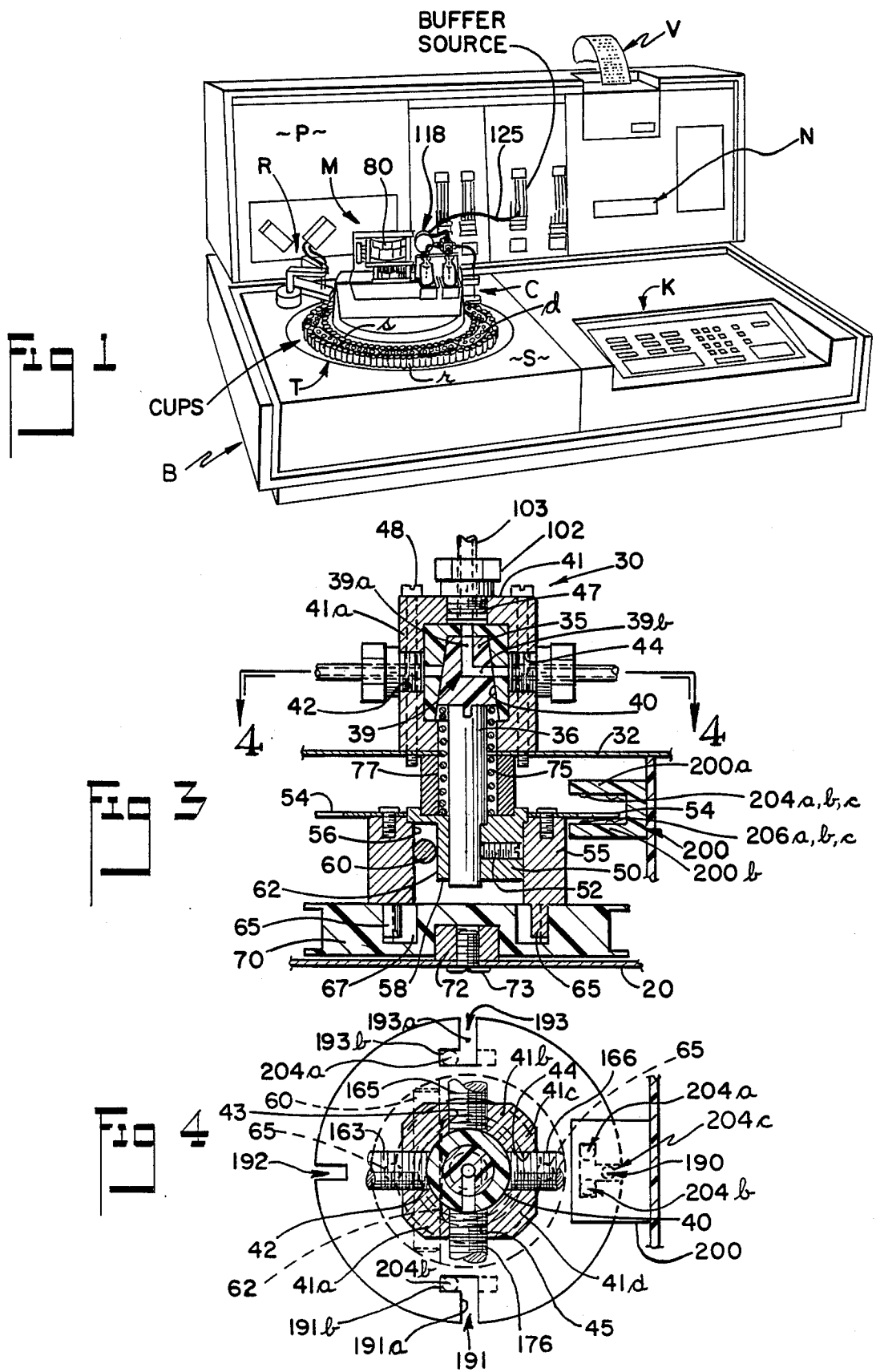

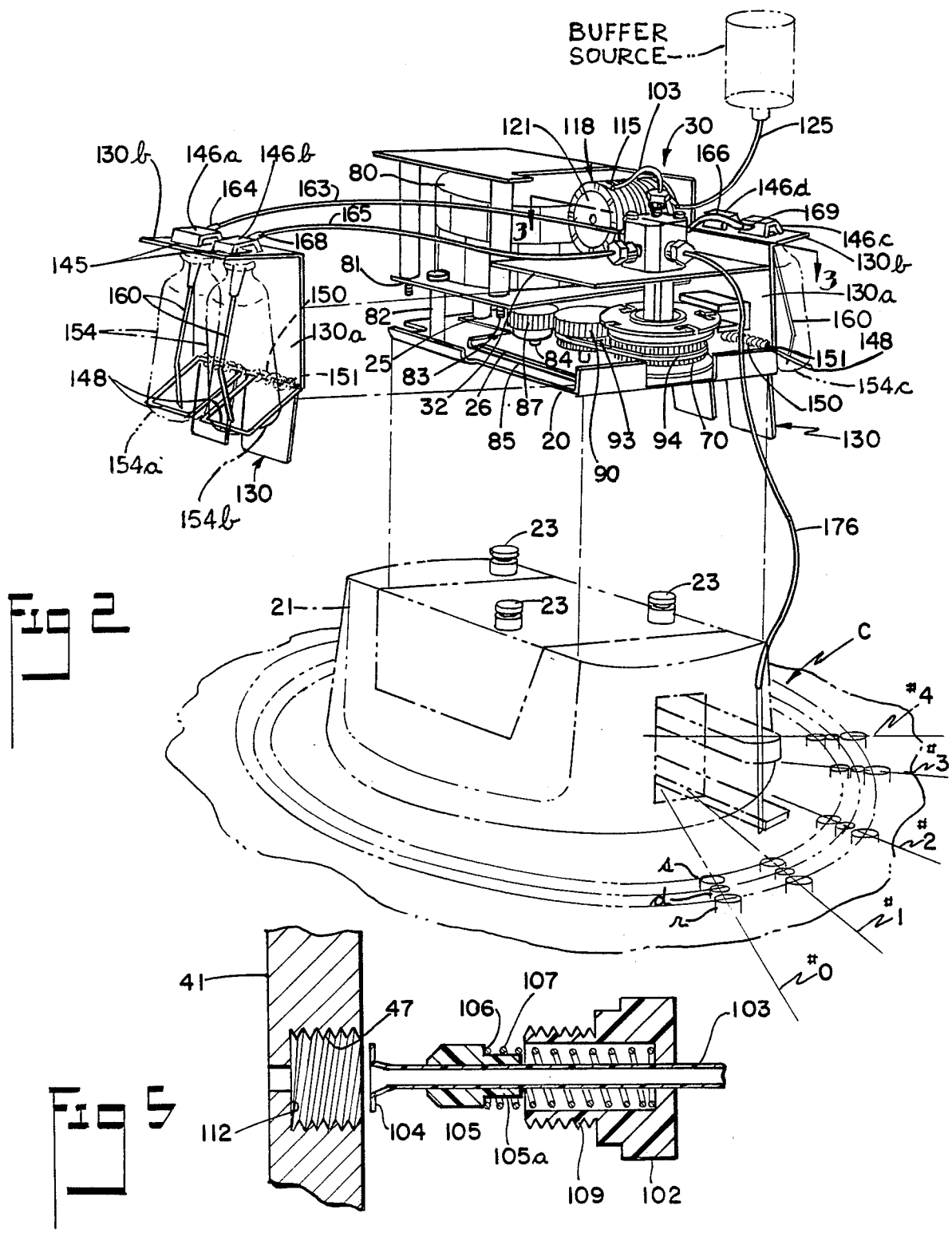

TEST MODULE

This invention relates to clinical analyzers, and more particularly to a test module or reagent handling device especially designed for use with a clinical analyzer for performing a plurality of biochemistry assays and immunoassays.

As will be hereinafter more fully described, the present configuration of test module is especially designed for use with a type of clinical analyzer such as the assignee's presently commercially available analyzer identified as its Impact 400 Clinical Chemistry Analyzer, but as will also be hereinafter understood, it is contemplated that the present test module is also adapted for use with other types of analyzers, and wherein the various modifications required to be made to the said module and/or the analyzer to adapt one to the other may be accomplished without departing from the inventive concepts as are more fully described hereinafter.

The present test module is primarily designed for use with the aforesaid analyzer to accurately serially analyze a plurality of individual samples of human serum or plasma. The analyzer, as more fully explained in the assignees' Technical and Operator's Manual presently available with said Impact 400 type of instrument is a spectroscope type of instrument, utilizing, as understood in the art, photometric and/or fluormetric measurement techniques.

Merely for purposes of the present disclosure, the test module of the present invention will be herein described in performing a serum or plasma immunoassay procedure wherein a plurality of serum samples are sequentially individually diluted, thence individually reacted with a suitable reagent material and/or materials and then serially presented to the spectroscopy analyzer for absorptive and/or fluormetric analysis.

In the performance of such clinical analysis an individual serum cup containing a human blood serum sample is positioned in the analyzer and presented to the test module whereat a portion of said sample is removed and thence transported to a diluter station at which said serum portion and a determined quantity of a suitable buffer or dilution material may be aspirated into a diluter cup wherein such mixture, serum and buffer or dilution material, are thoroughly mixed.

A predetermined portion of the diluted serum and buffer material of the diluted sample is then aspirated out of the diluter cup by said module and then dispensed by said module along with one or several reagent materials such as a suitable antibody enzyme and/or a suitable fluorescein drug reagent material into a reaction cup wherein the desired reaction therebetween occurs.

After a suitable incubation period, the reactivated sample is presented to the spectroscopic analyzer whereat the absorptive and/or fluormetric analysis is undertaken.

With the test module of the present invention a plurality of assays may thus be substantially serially automatically and accurately performed.

BRIEF DESCRIPTION OF THE DRAWINGS

FIG. 1 is a perspective view of an analyzer and the test module or reagent handling device of the present invention for use therewith mounted in its operative position on said instrument;

FIG. 2 is a perspective view of the test module of the present invention with certain of its components being illustrated in an exploded configuration;

FIG. 3 is a vertical longitudinal sectional view taken on line 3—3 of FIG. 2 and showing the internal construction of the control valve assembly and its drive;

FIG. 4 is a sectional view taken on line 4—4 of FIG. 3, and showing the several tubing or conduit connections to the control valve, and the encoding plate associated therewith; and FIG. 5 is a horizontal sectional view illustrating the connector assembly for connecting the tubing or conduit to each part of the valve assembly.

DESCRIPTION OF THE PREFERRED EMBODIMENT

With reference directed to FIG. 1 the present test module or reagent handling device is suited for use with the type of analyzer pictorially illustrated therein and known as the assignee's Impact 400 Clinical Spectrophotometer Analyzer presently commercially available in the art, and which is seen to comprise a desk type cabinet B having a generally horizontally disposed work platform S and a rear upstanding supporting panel P.

The platform S houses suitable computer control circuitry which, as will be understood in the art, is capable of programming the analyzer to automatically perform the test procedures such as are hereinafter described.

A turntable T is supported on the platform S and carries a plurality of cups or vessels in a particular array which are used in the performance of certain of said test procedures utilizing the test module of the present invention.

A dispensing probe C is supported over the turntable T at the dispensing position D and is movable, in a manner to be hereinafter fully explained, over the aforesaid cups or vessels to dispense the serum sample and associated buffer and reagent materials into and out of said cups in the performance of the biochemistry assays.

A keyboard K disposed within the platform S is utilized by the clinical technician to program the analyzer and thus to preselect the parameters of the test procedures to be undertaken and to initiate and to terminate the same in a manner well understood in the art.

A reading or testing station R is located near the left side of the platform S at which a predetermined volume of the material to be tested may be withdrawn from one of the cups of said array and presented to the spectrophotometer of the instrument wherein an absorbance and/or fluorscopic examination thereof is undertaken.

A suitable tape printer V and a visual digital display N carried within the panel P provides a permanent record as well as an instantaneous visual display of analytic results of the biochemistry assay undertaken.

The test module M of the present invention is mounted over the turntable T and the dispensing probe C and is operable with said probe C to dispense certain dilution and/or reagent materials into the test cups or vessels.

With reference now directed to FIGS. 1 and 2 in the present embodiment of analyzer instrument, the turntable T is circular in configuration and formed with three concentrically spaced sets or series of holes identified at $h_1$, $h_2$ and $h_3$, respectively. One hold from each series is centered on a single radius line of the turntable T and referred to herein as an assay test position identified for example, by a single numeral reference "1, 2, 3, 4, ... 0 etc."

For example, as best seen in FIG. 2 a single radius line 1 of the turntable extends through the center of one of the holes $h_1$, $h_2$ and $h_3$ of each series and is defined as test position "1". Similar test positions spaced radially about the center of the turntable are also identified by the reference numerals "2", "3", "4", ... "0" etc.

An open top serum cup s of the type disclosed in the assignee's copending application Serial No. filed July 30, 1982, is disposed in each hole of the innermost series of holes $h_1$ and is intended to accept a human serum sample which is to be analyzed.

A dilution cup d, of the type disclosed in the assignee's copending application, Serial No. filed on July 30, 1982, is disposed in each hole of the intermediate series of holes $h_2$, being thus radially spaced outwardly on its associated radius line from the serum cup s at said test position "1", "2", etc., and is intended to accommodate therein a predetermined portion of the serum sample taken from the serum cup at said position and which is dispensed therein along with a dilution material effective to provide therein a dilution of the said serum sample.

A reaction cup r, of the type also disclosed in the assignee's copending application Ser. No. 404,477 is disposed in each hole of the outermost series of holes $h_3$ in radial outwardly spaced relation to its associated dilution cup d at each said test position, and is intended to accommodate a predetermined volume of the diluted serum sample taken by the test module from its associated dilution cup at said test position and which is then dispensed into said reaction cup along with one or several reagent materials whereat a consequent reaction of said dispensed diluted serum and reagent materials occurs.

The turntable T is actuated in a step-by-step manner by a turntable drive provided with said instrument to present serially and sequentially the cups at each test position to the overlying dispensing probe C and test module whereby the above serum, dilution and reagent material dispensing procedure is repeated.

The reaction of the serum and reagent materials disposed in each reaction cup r continues during which time the turntable T is stepped in a clockwise direction as viewed in FIG. 1, and at the completion of a preselected "incubation period" the turntable T has carried said cup r to the instrument reading or testing station R. As aforementioned, a predetermined volume of the incubated serum-reagent mixture is then aspirated out of the reaction cup and placed into a cuvette of the instrument spectrophotometer whereat its absorptivity and/or fluorescence is measured, visually indicated and recorded by said instrument in a manner as will be understood.

With reference now directed to FIGS. 1 and 2, the test module or reagent handling device of the present invention, as aforesaid, is mountable on top of the turntable T in the position illustrated in FIG. 1, so as to be accessible to the underlying dispenser probe C, and for this purpose, said module includes a base platform or plate 20 which is generally rectangular in configuration and adapted to lie on the top surface of the housing 21 of the dispenser probe C. Suitable fastening means such as posts 23 carried on the housing 21 and which are adapted to project into apertures 25 in the base plate 20 and suitably locked therein by slidable lock plate 26 slidably disposed on plate 20 may be utilized to releasably secure the base plate 20 to said housing 21.

A dispensing turret valve assembly, as depicted in its entirety at 30, is mounted by bracket member 32 in an upright vertical position adjacent one end of plate 20 (right end as depicted in FIG. 1) in proximity to the dispensing probe C. Turret assembly 30 is operable in the manner to be described to selectively dispense serum sample, dilution material and several reagent materials into and out of the aforementioned cup units carried on the turntable T.

For this purpose, the turret valve assembly as best seen in FIG. 3, comprises a valve plug member 35 which is of truncated conical shape mounted on the upper end of shaft member 36. It is contemplated that plug member 35 and shaft member 36 may be made in one piece. Plug member 35, as best seen in FIG. 3 is provided with an internal channel 39 which is L-shaped in cross-section formed of connecting channel legs 39a and 39b. Plug member 35 is disposed centrally within a complementary cavity 40 formed in turret housing 41 which is basically of square cross-section as viewed in FIG. 2. Turret housing 41 is formed with a plurality of ports identified at 42, 43, 44 and 45, each of which is spaced 90° from its adjacent port on either side and is seen to project through one side wall of the housing to communicate at its inner end with the centrally disposed cavity 40. Housing 41 is also provided with a port 47 formed in its top wall as viewed in FIG. 3 and which projects downwardly centrally therethrough to connect at its inner end with the channel leg 39a formed in plug member 35.

The plug member 35 is intended to be rotated within the turret housing 41 to connect the channel leg 39b selectively with one of the ports 42, 43, 44 and 45 and thereby connect the latter with channel leg 39a.

As best seen in FIG. 3, the shaft member 36 is rotatably suspended between the aforementioned bracket member 32 and base platform 20. Turret housing 41 is fixedly supported on the upper surface of bracket member 32 being suitably attached thereto by fasteners 48.

Coupling 50 receives the lower end of shaft member 36 and is keyed thereto by pin 52 being thus rotatable therewith. A circular encoding plate 54 later to be referred to is secured to the upper face of coupling 50 and likewise is rotatable therewith.

A drive hub 55 has a centrally disposed recess 56 into which is disposed boss element 58 formed integrally on the underside of said coupling 50. Pin 60 extending sectorally through the drive hub 55 engages a flat coupling surface 62 formed on boss element 5S and thus drivingly interconnects the same.

A pair of driving pins 65 provided on the underside of drive hub 55 project downwardly therefrom and extend into apertures 67 formed in external gear element 70. Said gear element is rotatably supported on bearing 72 carried on the top surface of platform 20 being secured thereto by fastener 73.

A coil spring 75 disposed on shaft member 36 has its upper end engaging the underside of plug member 35 and its lower end disposed within retainer nut 77 suitably secured to the shaft member 36, being thus effective to urge the plug member 35 into pressure engagement with the complementary wall of housing cavity 40 and thereby provide a substantial liquid-tight relation therebetween.

With this turret assembly as thus described, rotation of gear element 70 is effective to cause a corresponding rotation to the plug member 35. Such rotation is caused by a stepping motor 80 FIG. 2 of conventional design supported on flat plate member 81, which, in turn, is supported on posts 82 and 83 in spaced relation above the platform 20. Shaft 84 of said stepping motor extends into the space 85 between platform 20 and plate member 81 and has a drive gear 87 securely attached thereto. Follower gear 90 is mounted on shaft 91 rotatably supported between said platform 20 and plate member 81, and thus drivingly meshes with drive gear 87.

Pinion gear 93 is carried on shaft 91 below follower gear 90 and is rotatably driven with said shaft.

A suitable endless drive belt 94 having internal drive teeth is placed over and meshes with gear element 70 and pinion gear 93 to drivingly connect said gear element 70 to said pinion gear.

With this assembly, upon the excitation of stepping motor 80, the valve plug member 35 is rotatable within the housing cavity 40 to selectively connect one of the ports 42-45 to channel leg 39b and hence to connect said selected port to channel leg 39a of said plug member.

In the present embodiment of test module, it is intended that each actuation of stepping motor 80 will cause a corresponding 90° rotation to the plug member 35.

As aforementioned, a suitable buffer or dilution material is to be dispensed by the test module along with a predetermined quantity of serum into a dilution cup d preparatory to the assay thereof.

For this purpose, the turret housing as best seen in FIGS. 3 and 5, is provided with entry port 47 formed in the top wall of said housing 41 and extending therethrough and communicating with the channel leg 39a of plug member 35.

A flanged nut 102, formed in its present configuration of a suitable plastic such as nylon, has one end of a flexible tube 103 projecting centrally therethrough and terminating in a flared end 104. A plug 105 is slidably disposed over the flared end 104 of said tube and is provided with stem portion 105a of reduced diameter to define annular shoulder 106 upon which seats one end of coil spring 107, the other end of said spring seating within the externally threaded boss 109 of said flanged nut 102. The flared end 104 of tube 103 is placed into entry port 47 and engages seat 112 provided at the inner end of said port. Upon threading the nut 102 into said port, the coil spring 107 provides suitable pressure against said flared end to provide a liquid-tight seal between it and seat 112.

The opposite end of tube 103, as seen in FIG. 2, connects to the output end of heater coil 115 of buffer heater 118 which comprises coil 115 wrapped around a spool shaped heated element 121 which is connected to the instrument control and operable to heat the buffer or dilution material passing therethrough to a temperature within a preferred range of 35° C. to 45°C. The buffer heater is disposed in close proximity to and behind the turret assembly 30, and supported above bracket member 32.

The inlet end of heater coil 115 is connected by tubing 125 to a suitable supply or buffer or dilution fluid such as distilled water carried in bottle B mounted on the instrument panel P.

Buffer fluid is manipulated for aspirating and dispensing by automatic pipetor/dilutor or reversably acutatable syringe of the analyzer which is effective to aspirate diluted serum out of a dilution cup and thence subsequently to dispense said diluted serum and a selected reagent material into a reaction cup carried on turntable or transport T.

For this purpose, a plate 130 is mounted on each side of the bracket member 32 and has a vertical wall portion 130a depending downwardly from said bracket and extending below the base platform 20. As seen in FIG. 2, each plate 130 is generally inverted L-shaped in cross-section, having a flat horizontally disposed short wall portion 130b projecting outwardly from its associated vertical wall portion 130a. As best seen in FIG. 2, each short horizontal wall portion 130b is provided with a pair of spaced apertures 145 into each of which is releasably disposed a coupling member, each of which is identified at 146a, 146b, 146c.

A pair of retainer clips 148, generally U-Shaped in configuration, is swingably attached at the opposed free ends thereof to a rod member 150 disposed behind the vertical wall portion 130a of each plate 130. Coil springs 151 carried on each rod member 150 are connectable to the aforesaid ends of each clip 148 being operable to urge said clips to extend substantially perpendicularly outwardly from the above wall portion 130b of said plate 130.

As seen in FIG. 2, each said clip is intended to be swung downwardly about its ends to permit the placement of a reagent bottle or the like, as identified at 154, 154a and 154b to capture the bottle between the coupling and the clip.

A length of tubing 160 which, in its present form, is metal has its upper end disposed in each coupling member 146a-146c, said tubing 160 projecting downwardly therefrom and into the bottle disposed therebelow. As seen in FIG. 2, the bottom portion of each said tubing 160 bends slightly inwardly towards the vertical wall portion 130a. In addition, the bottom end of each tubing 160 is formed at an angle of approximately 45° to the tubing longitudinal axis in order to prevent the tubing from being inadvertently sealed when it is held in place against the bottom of the reagent bottle 154, 154a and 154b.

As best seen in FIG. 2, a length of tubing 163 has its one end attached to one end of a short tube 164, the opposite end of which is connectable to coupling member 146a and communicates via said coupling with the tubing 160. The opposite end of tubing 163 is connected to inlet port 42 in the side wall 41b of turret housing 41 preferably by the same termination assembly as previously described to connect the heated buffer material via flexible tube 103 to entry port 47.

In like manner, one end of a flexible tube 165 and 166 is similarly connected to inlet ports 43 and 44 in side wall 41a and 41c respectively, of said turret housing 41, the opposite end of tube 165 connecting to one end of metal tube 168, the opposite end of which connects to coupling member 146b, and the opposite end of tube 166 similarly connecting with one end of metal tube 169, the opposite end of which connects to coupling member 146c.

In the present configuration of test module, the bottle 154d connecting with the remaining coupling member 146d in housing side wall 41d may be utilized as a waste position for certain test procedures whereby said bottle may alternately be connectable to one of the ports of the valve and positioned to collect the reaction sample at the completion of its analysis.

As best seen in FIG. 2, the turret housing 41 is connectable to the dispensing probe C, and for this purpose, one end of flexible tubing 176 is connected to housing port 45 utilizing the same tubing termination assembly as previously described herein with respect to entry port 47. The opposite end of said tubing 176 may be suitably connected to the dispensing probe C, and is of sufficient length to permit said probe to freely move to its several dispensing and/or aspirating positions, as will be presently described.

As previously mentioned, each actuation of the stepping motor 80 is intended to correspondingly rotate the valve plug member 35 ninety degrees (90°).

To accomplish this, the aforementioned encoding plate 54 carried on coupling 50 is provided with four slots, each having a particular configuration as identified at 190-193, respectively, each said slots being spaced 90° about the perimeter of said plate from its adjacent slot, as best seen in FIG. 4.

A sensor head 200, FIG. 3, is supported at one side of the encoding plate 54 and comprises two flat plates 200a and 200b disposed in spaced relation to each other on opposite sides of said plate 54 to permit the latter to freely pass therebetween. Sensor plate 200a carries a set of transmitter type transducers or sensors 204a, 204b, 204c disposed in predetermined spaced relation to each other and located on an imaginery circumferential line about the rotational center of valve plug member 35.

Sensor plate 200b carries three receiver-type transducers or sensor elements 206a, 206b and 206c, each of which is located directly below one of the transducers 204a, 204b and 204c, respectively, to thus define sensor pairs (204a, 206a), (204b, 206b) and (204c, 206c).

As best seen in FIGS. 3 and 4, the sensor pairs coact with the slots 190-193 in the encoding plate 54 to program the operation of the analyzer instrument as will be understood in analysis of a serum sample under test.

More particularly, as seen in FIG. 4, slot 190 is T-shaped in configuration with the stem of the T projecting radially into the plate 54 from its periphery and with the top or bar of the T extending perpendicularly thereto. The dimension of the slot 190 is such that when it is centered between the plates 200a and 200b of the sensor head 200, each sensor pair i.e. (204a, 206a; 204b, 206b; 204c, 206c) is likewise centered within the top or bar part thereof and adjacent opposite ends thereof as pictorially illustrated in FIG. 4 and are in their activated mode. In the present instrument operation, this position is also referred to as the "home position" or "dispenser probe" position in which position, as will be more fully described hereinafter, the probe C is operable to aspirate the test sample out of a sample cup and dispense said sample and one or more buffer materials into the dilution cup. Likewise, at said home position, the dispenser probe C is operable to aspirate a predetermined volume of diluted serum out of a dilution cup and to thereafter dispense said diluted serum along with one or more reagent materials serially into a reaction cup.

Encoding plate slot 191, as seen in FIG. 4, is of inverted L shape with its one leg 191a projecting radially into the plate 54 from its periphery and located 90° from the stem portion of T-shaped slot 190, said one slot leg 191a connecting at its inner end with its other leg 191b which extends perpendicularly and to the left as viewed in FIG. 4.

Slot 191 is dimensioned such that when it is centered between the plates 200a and 200b of sensor head 200 only sensor pairs 204b, 206b and 204c 206c are activated and sensor pair 204a, 206a is deactivated.

In the present instrument, when slot 191 is centered within sensor head 200 the instrument is programmed to provide a suitable antibody enzyme to the probe C preparatory to dispensing the same into a reaction cup.

Slot 192 is of rectangular configuration being spaced 90° from slot 191 on said plate 54 and projecting radially into the same from its periphery. Slot 192 is dimensioned such that when it is centered within the sensor head 200 both pairs (204a, 206a and 204b, 206b) of the aforesaid sensors are inactivated, while pair 204c, 206c is activated.

In the present instrument, when rectangular slot 192 is centered within the sensor head 200 the instrument is programmed to provide for a protein chemistry assay.

Slot 193, as seen in FIG. 4, is of reverse L-shaped configuration with its one leg 193a projecting radially inwardly into the plate 54 from its periphery, being located clockwise 90° from the rectangular slot 192, said slot leg 193a connecting at its inner end with its other leg 193b which projects perpendicularly and to the left therefrom. Slot 193 is dimensioned such that when it is centered within the sensor head 200 only the sensor pairs 204a, 206a and 204c, 206c are activated, and the instrument is programmed to provide for aspirating a fluorescein drug reagant material preparatory to dispensing the same into a reaction cup.

With the above described apparatus as incorporated for use with the analyzer instrument of the type identified as the assignee's Impact 400 instrument, a typical operational cycle is as follows.

As previously mentioned the Impact 400 type of instrument is a microprocessor controlled clinical chemistry analyzer which the operator utilizes the instrument keyboard to program and preselect the test analysis to be undertaken by said instrument.

In using the present test module with this type of instrument the microprocessor is interconnected with the module in a manner as is understood in the art whereby the buffer heater 118 as aforementioned, is connected into the microprocessor circuitry and controlled thereby so as to maintain the dilution liquid material passing therethrough at a temperature in the range of 35° C. to 45° C. Also, the stepping motor 80 is connected to said instrument control circuitry so as to be periodically actuatable to step the valve plug member 35 and sensor plate 54 selectively to one of its four positions during a sample test procedure.

Assuming, as viewed in FIG. 2, that serum cups s are disposed in the circle of holes $h_1$, each containing a serum sample to be analyzed, the dilution cups d are disposed in the circle of holes $h_2$ and the reaction cups r are disposed in the circle of holes $h_3$, and further assuming that the dispenser probe C is located over the "test position #1" as viewed in FIG. 1, and the test module has the encoding plate slot 190 disposed centrally within the sensor head 200 whereby the test module is at its "home position", the operator may actuate the microprocessor and initiate a typical assay whereby the dispense probe C moves downwardly into the serum cup s at test position #1. The reversable syringe of said instrument is then actuated to aspirate or withdraw a suitable volume of serum, as for example approximately 8 micro-liters, from said cup and up into the tubing 176 connecting with valve port 45. The probe C moves out over the dilution cup d at said test position #1 whereat the withdrawn serum sample and a suitable quantity of heated dilution material, for example approximately 400 micro-liters, from the dilution source are dispensed serially into said dilution cup to provide an approximate 50:1 dilution.

The probe C is then raised, the stepping motor 80 actuated to rotate the valve plug 35 and encoding plate 90° clockwise as viewed in FIG. 4 whereby the fluorescein drug reagent material in bottle 154b is connected to the valve plug member 35 and upon programmable actuation of the reversable syringe a predetermined volume (for example 20 micro-liters) of said reagent material is sucked into tubing 103. Concurrently, the turntable transport T is stepped clockwise as viewed in FIG. 2 to bring the last preceding test position #2 under the probe C. The probe C is then lowered into the reaction cup r at said test position #2 and concurrently stepping motor is actuated to rotate valve plug 35 and encoding plate 90° counterclockwise. The fluorescein drug reagent material is then dispensed into said reaction cup through tubing 103 and 176 along with a predetermined volume of dilution material from said dilution source to begin the incubation period for the diluted test serum sample in said reaction cup of test position #2.

The probe C is again raised, and the turntable transport T is reversably stepped counterclockwise as viewed in FIG. 2 to again locate said probe C over test position #1. At the same time the valve plug member 35 and encoding plate 54 are stepped by the actuation of stepping motor 80 90° counterclockwise as seen in FIG. 4 to locate encoding slot 191 between the plates of the sensor 200. Antibody enzyme in reagent bottle 154c is then drawn by the instrument syringe out of said bottle and into tubing 103.

The valve plug member 35 and encoding plate 54 are then stepped by stepping motor 80 clockwise 90° as viewed in FIG. 4 to return the encoding slot 190 between the plates of the sensor 200 or to the "home position".

The probe C is then extended into the dilution cup d at test position #1 whereat a predetermined volume of the diluted serum sample in said dilution cup is aspirated or sucked out thereof and into tubing 176.

The probe C is then extended out over the reaction cup r at said test position #1, the probe lowered into said cup and the diluted serum sample is dispensed into said reaction cup r serially with the antibody-enzyme from tubing 103 and a suitable volume of dilution material.

The probe C is again raised out of the reaction cup at test position ∩ 1 and the turntable transport T is stepped counterclockwise as viewed in FIG. 2 to locate the probe C at the next test position #0 at which the cycle just described is repeated.

After a preselected incubation period each reaction cup carrying the sample test mixture, i.e. serum sample, dilution material, antibody enzyme and fluorescein reagent material is moved individually by the turntable transport T to the reading station R whereat a predetermined volume of said mixture is aspirated out of said cup and presented to the spectrophotometer of said instrument wherein its absorption and/or fluorescent analysis is undertaken.

Having thus described a preferred embodiment of test module or reagent handling device of the present invention and the manner in which it is utilized with a typical clinical analyzer for performing a plurality of biochemistry assays and immunoassays, it will be realized that various modifications may be adapted thereto without departing from the inventive concepts as are set forth in the claims.

We claim:

1. A clinical analyzer instrument for spectrophotometrically assaying a liquid blood serum sample having; a reaction vessel, a sample vessel, a dilution vessel, a transport means for carrying the reaction vessel to a reading station, a dispensing probe, a means to withdraw and deposit a sample, and a microprocessor control means for dispensing serum samples, dilution materials, and liquid reagents into and out of these vessels; the improvement being a serial analyzer comprising:
    (a) a control valve means having a plurality of connection ports wherein a main connection port can communicate with any other single port;
    (b) a means connecting the valve means to the dispensing probe;
    (c) a means for connecting a diluent source to the control valve means;
    (d) a means for connecting at least one reagent source to the control valve means which is separate from the diluent source connection means;
    (e) a means for connecting the main port of the control valve means to the sample withdrawal and deposit means;
    (f) the transport means having a rotary motion, and separate serum, dilution, and reaction vessels being positioned thereon in a radial relationship;
    (g) a means for horizontally and vertically moving the dispensing probe whereby it can be positioned into a radially-spaced serum vessel to withdraw a sample, into a radially-spaced dilution vessel, first to deposit the sample and diluents, then to withdraw the diluted sample, and finally, into a radially-spaced reaction vessel to deposit at least a reagent and the diluted sample; and
    (h) a valve actuation means.

2. In a clinical analyzer as is defined in claim 1 and wherein means are provided for connecting at least two liquid reagent materials separately to the valve means.

3. The clinical analyzer of claim 1 wherein:
    (a) the transport means is annular; and
    (b) the dispensing probe, the sample withdrawal and deposit means, the control valve means, and the dispensing probe movement means are within the central opening of the annular transport means.

4. A clinical analyzer as defined in claim 1 and wherein the means in said valve means further comprises a valve plug member rotatably mounted in a housing.

5. A clinical analyzer as defined in claim 4 and wherein the valve plug member is provided with channel means selectively communicatable with each said port means upon rotation of said plug member.

6. A clinical analyzer as defined in claim 1 and wherein the valve actuating means comprises motor means.

7. A clinical analyzer as defined in claim 6 and wherein the motor means is a step motor actuatable to sequentially step the valve means along a predetermined path.

8. A clinical analyzer as is defined in claim 1 having an encoder means adapted to coact with the control valve means of said analyzer and operable to cause a predetermined sequence of actuation to said valve means.

9. A clinical analyzer as is defined in claim 8 and wherein the encoder means has sensor means adapted to coact with the control means.

* * * * *